United States Patent [19]

Sciaraffa et al.

[11] 4,062,874

[45] Dec. 13, 1977

[54] PHENOLIC STABILIZATION OF MALEIC ANHYDRIDE

[75] Inventors: Michael A. Sciaraffa, Bolingbrook; Gregory S. Cermak, Westmont, both of Ill.

[73] Assignee: Standard Oil Company (Indiana), Chicago, Ill.

[21] Appl. No.: 752,156

[22] Filed: Dec. 20, 1976

[51] Int. Cl.$^2$ ............................................ C07D 307/32
[52] U.S. Cl. ............................ 260/346.76; 260/346.74
[58] Field of Search ................. 260/346.8 M, 346.8 R

[56] References Cited

U.S. PATENT DOCUMENTS

| | | | |
|---|---|---|---|
| 3,056,805 | 10/1962 | Gleason | 260/346.8 R |
| 3,476,774 | 11/1969 | Zaweski et al. | 260/346.8 M |
| 3,586,703 | 6/1971 | Martinez et al. | 260/346.8 M |
| 3,975,408 | 8/1976 | Boyer et al. | 260/346.8 R |

FOREIGN PATENT DOCUMENTS 41-19405  11/1966  Japan ............................ 260/346.8 M Primary Examiner—Richard L. Raymond
Attorney, Agent, or Firm—William H. Magidson; Arthur G. Gilkes; William T. McClain

[57] ABSTRACT

Stabilization of maleic anhydride with 4,4′-di(hydroxyphenyl)alkanes or 4-alkylphenols.

5 Claims, No Drawings

PHENOLIC STABILIZATION OF MALEIC ANHYDRIDE

This invention relates to heat stabilization of maleic anhydride with 4,4'-di(hydroxyphenyl)alkanes or 4-alkylphenols. More particulary, this invention relates to the stabilization of maleic anhydride with Bisphenol A.

The literature is replete with patents directed to the stabilization of maleic anhydride since maleic anhydride is heat and light sensitive, i.e. it yellows with time and temperature. For the most part, the extent of yellowing depends on the quality of the maleic anhydride as well as the conditions of storage. While the mechanism and cause of the yellowing is not known, this yellowing has been blamed on parts per million level of impurities (reaction and/or processing contaminants and/or by-products) which may react themselves to give yellow impurities or catalyze the degradation of the maleic anhydride.

Normally, commercial maleic anhydride must pass two molten color specifications. The initial color of the maleic anhydride melt must be below a certain accepted value and the maleic anhydride melt must be heat stable for 2 hours at 140° C. Since maleic anhydride is sold in solid forms, as briquettes, tablets and pastilles, and in the molten form at around 60° C, the maleic anhydride must pass these color specifications, not only after manufacture, but also after extended storage and transportation at 60° C. Further, since chemical additives themselves are incapable of improving off-color maleic anhydride, maleic anhydride being stabilized must be of reasonably high quality.

The literature in many cases indicates contradictory results with the same stabilizers. The reason for this is not understood at this time but may be related to the history or method of producing the particular maleic anhydride since maleic anhydride can be produced by oxidation of benzene, saturated and unsaturated $C_4$ hydrocarbons (e.g. butane or butene) or as a by-product of naphthalene oxidation to phthalic anhydride. For example, while Halcon U.S. Pat. No. 3,586,703 indicates that sodium iodide is ineffective, Monsanto British specification No. 1,331,853 discloses the stabilization of maleic anhydride with halogen compounds broadly and illustrates the effectiveness of sodium diodide as a stabilizer for maleic anhydride, (both of these reference are incorporated by reference). Our own studies seen to confirm the conclusion of the Halcon Patent. As indicated above, the reason for these discrepancies is unclear and may be related to the method of producing the maleic anhydride, etc.

The general object of this invention is to provide a new class of heat stabilizers for maleic anhydride. Other objects appear hereinafter.

We have found that maleic anhydride can be heat stabilized with certain phenolic compounds, namely 4,4'-di(hydroxyphenyl)alkanes and 4-alkylphenols. For the purpose of this invention, the terms "heat stabilized" or "heat stable" are used to indicate that other things being equal, the maleic anhydride containing phenolic compound has a lower APHA (American Public Health Association Units in accordance with ASTM D1209-69) after being held at 140° C for 2 or more hours than maleic anhydride containing no phenolic stabilizer. The phenolic stabilizers useful in this invention include phenolic compounds having one OH moiety on each benzene ring and a saturated aliphatic group para to the OH moiety capable of providing the aforesaid improvement. If the phenolic compound contains two hydroxy moieties on a single benzene ring, such as present in a catechol or hyroquinone described in Mitsui Japanese No. 66-19405 of Nov. 10, 1966 or Mitsubishi Japanese No. 72-26766-R of July 19, 1972, there is a tendency for the formation of chromophores (color bodies) which are undesirable. Further, compounds having more than one aliphatic substituent seem to accelerate color formation. For example, both butylated hydroxy-toluene and 4,4'-methylene bis 2,6-di-(tertbutylphenol) accelerate color formation in maleic anhydride.

Suitable phenolic compounds useful in this invention can be represented by the formulas

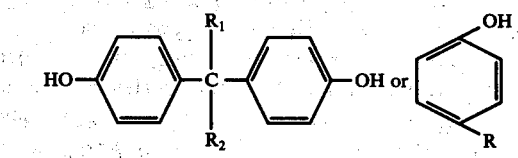

wherein R is an alkyl group of from 1 to 18 carbon atoms, such as methyl, ethyl, isopropyl, tertiary-butyl, tertiary-octyl, n-nonyl, tertiary-dodecyl, stearyl, etc., $R_1$ and $R_2$ are independently hydrogen or alkyl groups of from 1 to 9 carbon atoms and $R_1$ and $B_2$ contain a total of 0 to 9 carbon atoms. $R_1$—C—$R_2$ can also be viewed as a methylene group when both $R_1$ and $R_2$ are hydrogen or when at least one of $R_1$ and $R_2$ is an alkyl group, $R_1$—C—$R_2$ is an alkylidene group of from 2 to 10 carbon atoms (such as ethylidene, isopropylidene, propylidene, dodecylidene, etc.). Suitable compounds include 4-tertiary-butylphenol, 4-tertiaryoctylphenol, paranonylphenol, paradecylphenol, paradodecylphenol, parastearylphenol, Bisphenol A (4,4'-bisphenol-2,2'-propane), 4,4'-di(hydroxyphenyl) 2,2'-decane, etc. The preferred phenolic compounds useful in this invention are the diphenolic compounds and particularly Bisphenol A which are approximately twice as effective on a weight basis as the monohydroxy phenolic compounds. The diphenolic compounds have the additional advantage that during polyesterification they function as diols and do not function as chain terminators like the monohydroxy phenolics.

One or more phenolic compounds can be used in a total stabilizing concentration of about 1 to 200 parts per million (ppm) based on the concentration of maleic anhydride. Generally the preferred phenolic compounds can be utilized in a concentration of about 1 to 50 parts per million based on the weight of the maleic anhydride. It is desirable to use the minimum concentration of phenolic stabilizer consistent with the degree of stabilization desired since, as the concentration of phenolic increases above about 100 ppm, there is a tendency for the maleic anhydride to discolor about 5 APHA units due to the presence of excess phenolic.

The maleic anhydride utilized in this invention can be produced by any process suitable for the production of maleic anhydride. However, we prefer to use maleic anhydride produced by the oxidation of butane, such as that described in Boghosian U.S. Pat. No. 3,862,146, which is incorporated by reference. In any case the maleic anhydride should be relatively pure prior to the addition of the stabilizer. Generally, the stabilizer can be added to molten maleic anhydride shortly after the maleic anhydride is distilled for most of its impurities and by-products formed in the oxidation of the particular organic precursor.

The anhydrous stabilizer can be added to the maleic anhydride neat or in a diluted form. On a commercial basis dilution of the preferred phenolic compound is not necessary since they are very soluble in molten maleic anhydride. However, if desired, the phenolic can be dissolved in methyl ethyl ketone, methanol, etc.

The following examples are merely illustrative and should not be construed as limiting the scope of the invention.

EXAMPLE 1

After 266 grams of solid maleic anhydride, produced by the method of U.S. Pat. No. 3,862,146, was dissolved at 140° F in a 250 ml Erlenmeyer flask containing a magnetic stirrer bar, Bisphenol A stabilizer was added to the maleic anhydride. The molten maleic anhydride was stirrer and then added to a Nesslerimeter test tube and filled to the 210 mm high liquid level. Immediately thereafter the initial molten color was measured by visual comparison with standard APHA solutions in Nesslerimeter tubes according to ASTM D 1209-69 (platinum-cobalt scale). After reading, the tube was placed in a 284° F (140° C.) heater and capped with a 10-milliliter beaker to prevent contamination and the tube heater was covered with a 100 × 190 milliliter crystallization dish. The heat stable colors were read after 2, 4, and 24 hours. The results are set forth below in Table I. Multiple runs in the Table indicate the use of different batches of maleic anhydride.

Table 1

| Stabilizer | PPM | Initial | Molten Color APHA Hours at 140° C | | |
|---|---|---|---|---|---|
| | | | 2 | 4 | 24 |
| Blank | | 15 | 75 | 200 | 1500 |
| Bisphenol A | 10 | 15 | 25 | 45 | 250 |
| Bisphenol A | 50 | 15 | 35 | 55 | 275 |
| Blank | | 20 | 75 | 225 | 1300 |
| Bisphenol A | 10 | 20 | 30 | 40 | 115 |
| Bisphenol A | 50 | 20 | 35 | 45 | 125 |
| Blank | | 10 | 20 | 80 | 1500 |
| Bisphenol A | 10 | 10 | 20 | 25 | 100 |

The above data indicates that B is phenol A is an excellent maleic anhydride stabilizer.

EXAMPLE II

Example I was repeated except that Bisphenol A was replaced with 50 ppm 2,2-bis(4-hydroxyphenyl) butane. The results are set forth below in Table II.

Table II

| Stabilizer | PPM | Molten Color APHA Hours at 140° C | | |
|---|---|---|---|---|
| | | Initial | 2 | 24 |
| Blank | | 5 | 30 | 500 |
| 2,2-bis(4-hydroxy- | | | | |

Table II-continued

| Stabilizer | PPM | Molten Color APHA Hours at 140° C | | |
|---|---|---|---|---|
| | | Initial | 2 | 24 |
| phenyl) butane | 50 | 15 | 25 | 70 |

The above data indicates that 2,2-bis(4-hydroxyphenyl) butane is an excellent maleic anhydride stabilizer.

EXAMPLE III

Example I was repeated except that Bisphenol A was replaced with 100 ppm 4-t-butylphenol. The results are set forth below in Table III.

Table III

| Stabilizer | PPM | Molten Color APHA Hours at 140° C | | |
|---|---|---|---|---|
| | | Initial | 2 | 24 |
| Blank | | 15 | 30 | 500 |
| 4-t-butylphenol | 100 | 20 | 25 | 60 |

The above data indicates that 4-butylphenol is an excellent maleic anhydride stabilizer.

We claim:

1. A composition consisting essentially of maleic anhydride and a heat stabilizing concentration of from 1 to 200 ppm based on the concentration of maleic anhydride of at least one phenolic compound selected from the group consisting of 4-alkylphenols having the structure

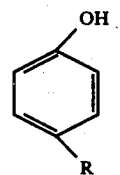

and 4,4'-di(hydroxyphenyl) alkanes having the structure

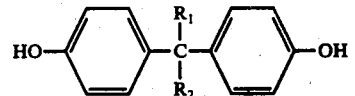

wherein R is an alkyl group of from 1 to 18 carbon atoms, $R_1$ and $R_2$ are independently hydrogen, alkyl groups of from 1 to 9 carbon atoms and $R_1$ and $R_2$ contain a total of 0 to 9 carbon atoms.

2. The composition of claim 1 wherein said phenolic compound is a 4,4'-di(hydroxyphenyl) alkane.

3. The composition of claim 2 wherein said phenolic compound comprises Bisphenol A.

4. The composition of claim 1 wherein said phenolic compound is a 4-alkylphenol.

5. The composition of claim 4 wherein said 4-alkylphenol compound comprises 4-tertiary-butylphenol.

* * * * *